United States Patent [19]

Wegmann

[11] Patent Number: 5,594,100
[45] Date of Patent: Jan. 14, 1997

[54] EPITOPE FOR PREVENTION OF TYPE I DIABETES

[75] Inventor: Dale R. Wegmann, Denver, Colo.

[73] Assignee: Regents of the University of Colorado, Boulder, Colo.

[21] Appl. No.: 394,004

[22] Filed: Feb. 22, 1995

[51] Int. Cl.[6] ............................ A61K 38/28; C07K 77/00
[52] U.S. Cl. ........................................... 530/303; 530/326
[58] Field of Search ................................... 530/303, 326; 514/3, 14

[56] References Cited

PUBLICATIONS

Llarde, A. et al., "Treatment of non–insulin–dependent diabetes mellitus and its complications", Drugs & Aging 4(6):470–491, 1994. See entire article.

Primary Examiner—Christine M. Nucker
Assistant Examiner—Benet Prickril
Attorney, Agent, or Firm—Frederick W. Pepper

[57] ABSTRACT

The present invention encompasses peptides derived from the 15 residue peptide 9-23, Ser-His-Leu-Val-Glu-Ala-Leu-Tyr-Leu-Val-Cys-Gly-Glu-Arg-Gly (SEQ ID NO:1), of the B chain of insulin. Peptides of the present invention are capable of acting as tolerogens for preventing type I diabetes.

1 Claim, 7 Drawing Sheets

Fig. 1A

| Sequence | Chain |
|---|---|
| G-I-V-D-Q-C-C-T-S-I-C-S-L-Y-Q-L-E-N-Y-C-N | A Chain |
| G-I-V-D-Q-C-C-T-S-I-C-S-L-Y-Q | A:1-15 |
| C-T-S-I-C-S-L-Y-Q-L-E-N-Y-C-N | A:7-21 |
| F-V-K-Q-H-L-C-G-S-H-L-V-E-A-L-Y-L-V-C-G-E-R-G-F-F-Y-T-P-M-S | B Chain |
| F-V-K-Q-H-L-C-G-S-H-L-V-E-A-L | B:1-15 |
| S-H-L-V-E-A-L-Y-L-V-C-G-E-R-G | B:9-23 |
| Y-L-V-C-G-E-R-G-F-F-Y-T-P-M-S | B:17-30 |

B:9-23    Murine Insulin II    S-H-L-V-E-A-L-Y-L-V-C-G-E-R-G

TT:830-843    Tetanus Toxin    Q-Y-I-K-A-N-S-K-F-I-G-I-T-E

Fig. 2A

EPITOPE FOR PREVENTION OF TYPE I DIABETES

The U.S. Government has a paid-up license in this invention and the right in limited circumstances to require the patent owner to license others on reasonable terms as provided for by the terms of Grant Nos. DK46621 and DK47298 awarded by the National Institutes of Health.

FIELD OF THE INVENTION

The present invention relates to a peptide and substitution analogs useful as toleragens for the prevention of diabetes.

BACKGROUND OF THE INVENTION

It is now established that insulin-dependent diabetes mellitus (IDDM) is an autoimmune disorder in which the insulin-producing beta cells are specifically destroyed. Overt diabetes is often preceded by the appearance of circulating antibodies specific to insulin (IAAs) [Palmer et al., Science 222: 1337 (1983)]. The nonobese diabetic (NOD) mouse develops IDDM with many similarities to the human disease and is considered to be a good model of type I diabetes [Makino et al., Exp. Anim. 29(1): 1 (1980)]. IAAs have also been found to be present in NOD mice [Reddy et al., Diabetologia 31: 322 (1988); Ziegler et al., Diabetes 38: 358 (1989)], and it has been suggested an immune response to insulin is the rate limiting step in development of diabetes [Eisenbarth et al., J. Autoimmunity 5 (Supplement A): 241 (1992)].

The NOD mouse develops insulin dependent diabetes as a consequence of spontaneous destruction of the insulin-producing pancreatic islet β-cells [Makino et al., Exp. Anim. 29 (1): 1 (1980)] and T cells are the major mediators of this β-cell destruction [Ogawa et al., Biomed. Res. 6(2): 103 (1985); Makino et al., Exp. Anim. 35(4): 495 (1986); Koike et al., Diabetes 36: 539 (1987); Wicker et al., Diabetes 35: 855 (1986); Bendelac et al., J. Exp. Med. 166: 823 (1987); Miller et al., J. Immunol. 140(1): 52 (1988)]. While a number of investigators have isolated and characterized panels of islet-specific T cell clones [Haskins et al., Diabetes 37(10): 1444 (1988); Haskins et al., Proc. Natl. Acad. Sci. U.S.A. 86: 8000 (1989); Nakano et al., J. Exp. Med. 173: 1091 (1991); Reich et al., Nature 341: 326 (1989); Haskins and McDuffie, Science 249: 1433 (1990); Christianson et al., Diabetes 42: 44 (1993); Shimizu et al., J. Immunol. 151: 1723 (1993)], there is little information with regard to the identity of the antigens recognized by these clones. Analysis of a panel of nominally islet-specific T cell lines and clones established from islet-infiltrating lymphocytes obtained from female NOD mice revealed that 22 of 40 (55%) responded to porcine insulin [Wegmann et al., Eur. J. Immunol. 24:1853 (1994)].

Further research of this spontaneously arising T cell response to insulin should provide information on the role of these cells in beta cell damage, epitopes of insulin that are recognized by insulin-specific T cells, and the effect of administration of insulin on the T cell response to insulin.

Studies now show that prophylactic insulin therapy can prevent diabetes in the NOD mouse [Atkinson et al., Diabetes 39:933 (1990); Zhang et al., Proc. Natl. Acad. Sci. U.S.A. 88:10252 (1991)]. Prophylactic insulin therapy is also being used in humans at risk for IDDM [Keller et al., Lancet 341(8850): 927 (1993)].

SUMMARY OF THE INVENTION

The present invention relates to peptides and analogs thereof derived from the 15 residue peptide 9-23, Ser-His-Leu-Val-Glu-Ala-Leu-Tyr-Leu-Val-Cys-Gly-Glu-Arg-Gly (SEQ ID NO:1), of the B chain of insulin which are capable of acting as toleragens for preventing type I diabetes.

The present invention relates to peptides comprising sequential subsets from within the sequence, Ser-His-Leu-Val-Glu-Ala-Leu-Tyr-Leu-Val-Cys-Gly-Glu-Arg-Gly (SEQ ID NO:1), which are capable of acting as toleragens for preventing type I diabetes.

The peptides of the present invention have the utility as tolerogens for the preventing type I diabetes in mammals.

Another aspect of the invention relates to pharmaceutical compositions containing peptides of the present invention as the active ingredient in a pharmaceutically acceptable medium.

The invention also relates to methods for preventing type I diabetes.

DESCRIPTION OF FIGURES

These and other objects, features and many of the attendant advantages of the invention will be better understood upon a reading of the following detailed description when considered in connection with the accompanying drawings:

FIG. 1A shows a set of overlapping 15 residue synthetic peptides based on the primary structure of murine insulin A and B chains against which T cell clones and lines were tested for proliferative responses.

FIG. 2A represents the amino acid sequence of the insulin and tetanus toxin peptides.

DETAILED DESCRIPTION OF THE INVENTION

It has been found that the destruction of beta cells, in the NOD mouse model and in humans, by T cells leads to type I or insulin-dependent diabetes. T cells, that infiltrate islets during the progression of the disease and engage in beta cell destruction, are isolated and characterized. The insulin-specific T cells are a major component of these infiltrating cells. A set of synthetic peptides were designed that covered the entire sequence of the A and B chains of mouse insulin. These peptides were tested for antigenicity using a panel of insulin-specific T cells. All the antigenic activity resides in one 15 residue peptide from the center of the B chain of insulin. The sequence of this peptide is: Ser-His-Leu-Val-Glu-Ala-Leu-Tyr-Leu-Val-Cys-Gly-Glu-Arg-Gly (SEQ ID NO:1). This peptide and all possible analogs are useful as tolerogens for treating mice and other mammals to delay the onset of type I diabetes and/or ameliorate or prevent the disease.

Figure 1B:
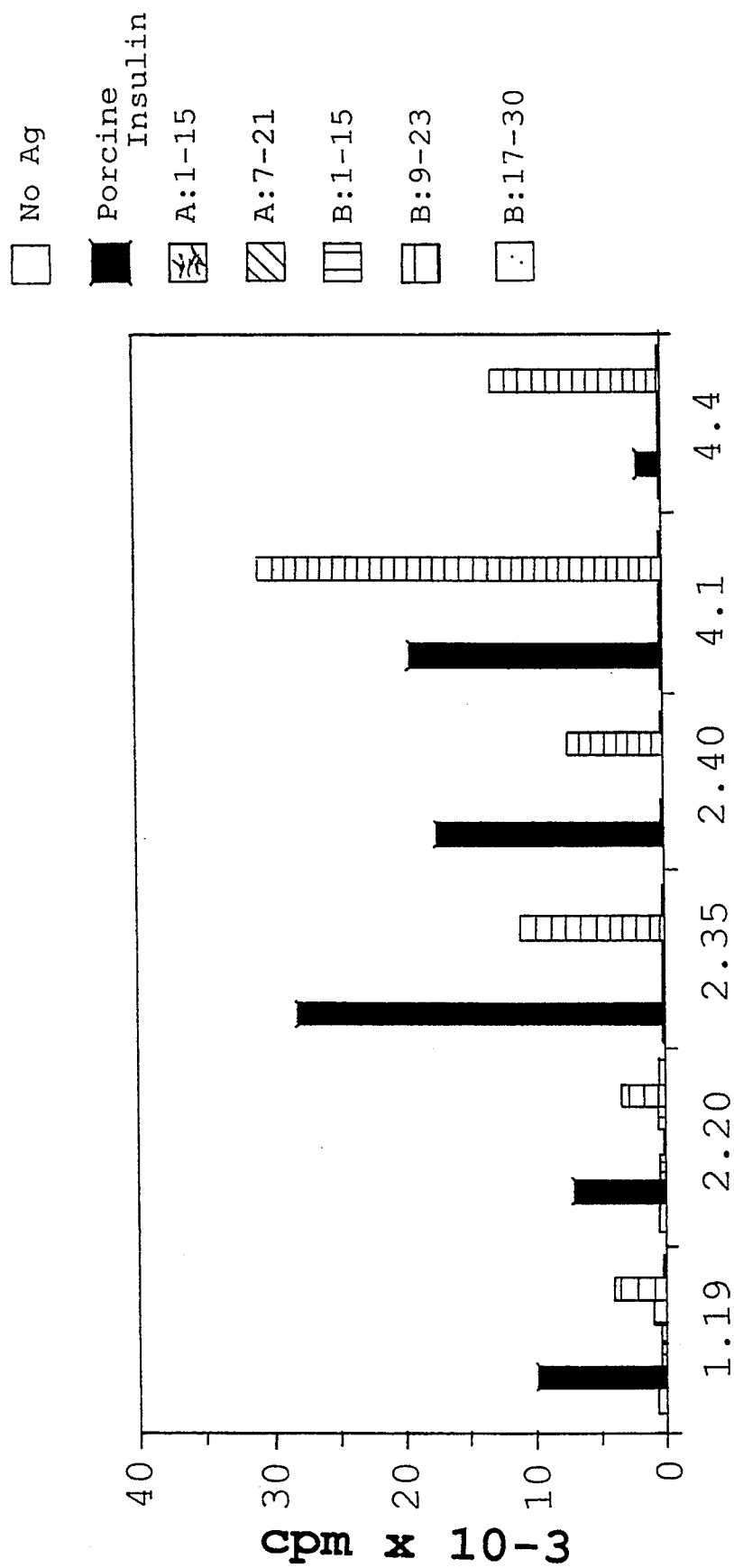
FIG. 1B is a graph showing the proliferative responses of insulin-specific PD12 T cell clones to porcine insulin and insulin peptides.

Identification of a Dominant Peptide Epitope for the Spontaneous T Cell Response to Insulin in NOD Mice A set of overlapping 15 residue synthetic peptides based on the primary structure of mouse insulin was used to localize the epitopes recognized by the panel of insulin-specific clones (FIG. 1A). Mouse insulin is produced in two isoforms which differ by 2 amino acids [Lomedico et al., *Cell* 18: 545 (1979); Wentworth et al., *J. Molecular Evolution* 23: 305 (1986)]. Synthetic peptides from both isoforms I and II were tested. The results, shown in FIG. 1B, indicate that all six clones responded only to the peptide that encompasses residue 9-23 of the insulin B chain (B:9-23) and were unresponsive to the other peptides in the panel. Although the data are shown only for the responses to insulin isoform II peptides, the peptide B:9-23 from insulin isoform I, which has a proline residue substituted at position 9, appears to be of equal potency in stimulation of the clones.

Figure 1C:
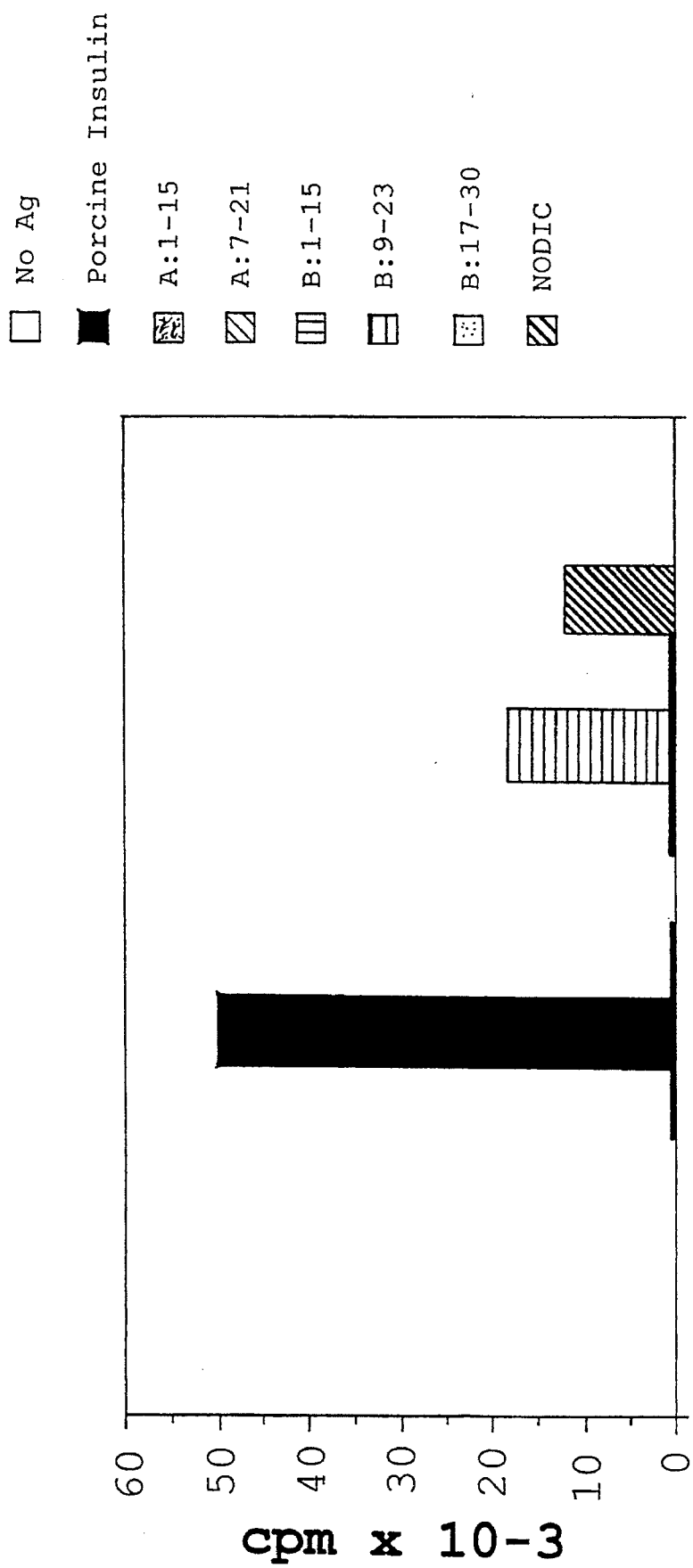
FIG. 1C is a graph showing the proliferative responses of the NOD islet cell-specific T cell line PD12-4 (IC) to porcine insulin, insulin peptides and NOD islet cells (NOD IC).

To determine if this peptide was the dominant epitope, a number of uncloned insulin-reactive T cell lines were tested for responsiveness to the set of overlapping peptides. These uncloned lines were heterogeneous, presumbably composed of diverse clonotypes. Therefore, they have specificities that would not appear in a panel of six randomly selected clones. These lines were propagated with irradiated NOD spleen cells and irradiated NOD islet cells. Thus, in vitro selection toward a particular peptide would not be expected. The results indicated that the response to insulin by islet-specific T cell line, PD12-4(IC), was directed entirely toward B:9-23 (FIG. 1C). Similarly, the other islet-specific T cell lines, that were tested, exhibited responses only to B:9-23, with no detectable responses to the other peptides. These data indicate that the spontaneous T cell response to insulin in the NOD mouse is, within the limits of detection, directed exclusively toward epitopes residing in the peptide B: 9-23.

Acceleration of Development of Diabetes in Young NOD Mice by Insulin-Specific T Cell Clones.

Adoptive transfer experiments have been used by others to assess the in vivo activity of islet-specific T cells [Haskins and McDuffie, *Science* 249: 1433 (1990); Nakano et al., *J. Exp. Med.* 173: 1091 (1991); Reich et al., *Nature* 341: 326 (1989); Shimizu et al. *J. Immunol.* 151: 1723 (1993)]. In one model, young NOD mice (<3 weeks of age) were shown to be susceptible to acceleration of diabetes by either T cell enriched spleen cells or by islet-specific T cell clones obtained from diabetic NOD mice [Bendelac et al., *J. Exp. Med.* 166: 823 (1987); Haskins and McDuffie, *Science* 249: 1433 (1990)]. When the insulin-specific clones were injected into young (6–14 days old) NODbdc mice, all were found to be capable of acceleration of the disease process (Table 1), albeit with considerable heterogeneity in the incidence of overt diabetes induced by each of the clones. In contrast, none of the islets of carrier (HBSS) injected control litter mates developed diabetes, nor did recipients of clone NKLH-1.5, a control CD4⁺T cell clone specific for keyhole limpet hemocyanin (KLH) and restricted by I-A$^{g7}$ (Table 1). Histological examination of pancreatic sections from mice which developed diabetes showed extensive intra-islet infiltration of the pancreatic islets by mononuclear cells and islet damage. Likewise, those mice receiving insulin-specific T cell clones which did not develop overt diabetes also showed extensive insulitis and islet damage. On the other hand, the islets of HBSS injected mice and recipients of clone NKLH-1.5 showed either no insulitis or minor per-islet infiltrates typical of NOD mice in this age group. The ability of these insulin-specific T cells to accelerate disease is clearly somewhat variable, but similar variability has been reported by others [Haskins and McDuffie, *Science* 249: 1433 (1990)]. Clone PD12-4.4 was transferred to young NOD mice in two separate experiments (Table 1). Although none of the recipients developed overt diabetes in the first experiment, histological examination revealed extensive insulitis and islet damage. In the second experiment one of six mice became overtly diabetic. The remainder again exhibited extensive infiltration and beta cell damage as assessed by histological examination. Despite the variability observed between individual clones, the overall results indicate that these insulin-specific T cells were diabetogenic in vivo.

TABLE 1

ACCELERATION OF DIABETES IN YOUNG NOD MICE BY INSULIN-SPECIFIC T CELL CLONES

| Clone | Antigen | Age | Diabetes Incidence Control | Diabetes Incidence T Cells | Day Post-Injection of Onset of Diabetes |
|---|---|---|---|---|---|
| 1.19 | B:9-23 | 8 | 0/4 (0%) | 4/6 (67%) | 12, 12, 14, 17, >47 (x2) |
| 2.20 | B:9-23 | 6 | 0/2 (0%) | 3/4 (75%) | 12, 12, 28, >52 |
| 2.35 | B:9-23 | 9 | 0/4 (0%) | 1/3 (33%) | 19, >47 (x2) |
| 2.40 | B:9-23 | 8 | 0/3 (0%) | 2/5 (40%) | 21, 24, >47 (x3) |
| 4.1 | B:9-23 | 13 | 0/5 (0%) | 4/5 (80%) | 17, 17, 29, 30*, >42 |
| 4.4 | B:9-23 | 14 | 0/5 (0%) | 0/5 (0%) | >38 (x5) |
|  |  | 12 | 0/3 (0%) | 1/6 (17%) | 21, >54 (x5) |
| NKLH-1.5 | KLH | 6 | 0/2 (0%) | 0/4 (0%) | >37 (x4) |

NODbdc mice were injected intraperitoneally at 7–14 days of age with 1.0–10⁷ insulin-specific PD12 T cell clones in HBSS. NKLH-1.5, a I-A$^{g7}$ restricted KLH-specific T cell clone, was injected as a T cell control. Vehicle control mice received an intraperitoneal injection of HBSS. The mice were considered diabetic after two consecutive blood glucose values above 10 mmol/L. *One mouse showed hyperglycemia for two consecutive blood glucose readings, but returned to normal after this transient hyperglycemic episode.

Adoptive Transfer of Diabetes to NOD/LtSz-scid (NOD-scid) Mice by Insulin-Specific T Cell Clones The NODscid mouse has undetectable levels of mature, functional B and T lymphocytes. Thus, it develops neither insulitis nor diabetes [Prochazka et al., *Proc. Nat. Acad. Sci.*

U.S.A. 89: 3290 (1992)]. This is a condition which makes this strain useful for the adoptive transfer of lymphocytes as a means of assessing the in vivo function of transferred populations. The fact that these mice are devoid of mature T and B cells allows the unambiguous demonstration of diabetogenic function by transferred T cells without the complications introduced by the presence of a host immune system. Recent studies have demonstrated that spleen cells from diabetic and pre-diabetic NOD mice could adoptively transfer diabetes in the NODscid mice [Christianson et al., Diabetes 42:44 (1993)]. It has been previously reported that islet-specific T cell clones known not to be insulin-specific were capable of adoptive transfer of diabetes to NODscid recipients [Wegmann et al., J. Autoimmun. 6: 517 (1993)]. All six insulin-specific T cell clones were tested for the capacity to mediate either overt diabetes or insulitis and beta cell damage in NODscid recipients. The results of these experiments indicate that only clone PD12-4.4 was capable of causing diabetes in the NODscid mice (Table 2). Furthermore, whereas NODscid recipients of clone PD12-4.4 had extensive infiltration and beta cell damage upon histological examination, recipients of the other five clones exhibited little, if any, islet infiltration.

TABLE 2

ADOPTIVE TRANSFER OF DIABETES IN NODscid MICE BY INSULIN-SPECIFIC T CELL CLONES

| Clone | Antigen | Diabetes Incidence | Day of Onset of Diabetes (post-1st injection) |
|---|---|---|---|
| 1.19 | B:9-23 | 0/2 (0%) | >60, >60 |
| 2.20 | B:9-23 | 0/3 (0%) | >60, >60, >60 |
| 2.35 | B:9-23 | 0/2 (0%) | >60, >60 |
| 2.40 | B:9-23 | 0/3 (0%) | >60, >60, >60 |
| 4.1 | B:9-23 | 0/4 (0%) | >60, >60, >60, >60 |
| 4.4 | B:9-23 | 12/12 (100%) | 7, 9, 10, 11, 11, 12, 15, 15, 16, 28, 28, 28 |
| PD6-11.6 | GAD Peptide | 0/2 (0%) | >45, >45 |

NODscid mice were injected intraveneously on 2–3 occasions at 2 week intervals with $1.0 \times 10^7$ insulin-specific PD12 T cell clones in HBSS. PD-11.6, an I-A$^{g7}$ restricted human glutamic acid decarboxylase (GAD) peptide-specific T cell clone, was injected as a T cell control. Unmanipulated NODscid mice never develop diabetes and are considered historical controls. The mice were considered diabetic after three consecutive blood glucose values above 10 mmol/L.

NODbdc mice were obtained from the colony at the Barbara Davis Center and NODscid founder mice for the BDC colony were obtained from Dr. L. Shultz (Jackson Laboratories, Bar Harbor, Me.). NODbdc mice were kept under specific pathogen-free conditions and the NODscid mice under sterile conditions.

Porcine insulin (Sigma Chemical Co., St. Louis, Mo.) was used for testing the specificity of the insulin-specific T cell lines and clones. A panel of synthetic peptides based on the primary structure of murine insulin was obtained (Cambridge Research Biochemicals, Northwich, Cheshire UK) to map epitope specificity of the insulin-specific T cells.

Isolation of insulin-specific T cell clones were carried out according to the procedure described in Wegmann et al., Eur. J. Immunol. 24(8): 1853 (1994). Briefly, islets isolated from collagenase digested pancreata were digested into single cell suspensions with trypsin (GIBCO BRL, Gaithersburg, Md.). Then islet-specific T cell lines were established from these suspensions by in vitro stimulation with $2.0 \times 10^4$ irradiated (3500R) NOD islet cells as antigen and $2.0 \times 10^7$ irradiated (3500R) NOD spleen cells in 20 ml DMEM (GIBCO BRL, Gaithersburg, Md.) supplemented to 10% with FBS (HyCLone Laboratories, Logan, Utah) and with PMA induced EL-4 supernatant (EL-4 SN) as a source of IL-2 (DMEM/FBS/EL-4). Clones were identified as insulin-specific by proliferation assays using porcine insulin as the antigen. The insulin-specific T cell clones were propagated by co-culture of $5.0 \times 10^5$ cells from the clone with $2.0 \times 10^7$ irradiated NOD spleen cells and 25 µg/ml (4.2 µM) porcine insulin in 20 ml DMEM/FBS/EL-4 on a 14 day cycle.

Proliferation assays of T cell lines and clones were performed by co-culture of $2.5 \times 10^4$ T cells with $1.0 \times 10^6$ irradiated (3500R) NOD spleen cells in the presence of antigen. Where indicated, $1.0 \times 10^4$ irradiated NOD islet cells, 100 µg/ml (16.7 µM) porcine insulin, or 50 µg/ml (26.3 µM) synthetic insulin peptides were added as antigen. Cultures were set up in duplicate in a total volume of 0.2 ml DMEM/FBS per well in flat bottomed 96-well microculture plates. The cultures were incubated for 72 hours with a pulse of 1.0 µCi [$^3$H]thymidine per well 6 hours prior to harvest. Proliferation is represented as mean c.p.m.

For the adoptive transfer of diabetes by T cell clones, insulin-specific T cell clones were prepared for injection by culture with antigen/APC for 4 days using the standard conditions described above for the culture of insulin-specific T cell clones. On the fourth day after stimulation the contents of the original culture flask were transferred to a larger volume medium supplemented with EL-4 SN and cultured for an additional 10 days. After this expansion the cells were collected, washed in HBSS and injected intraperitoneally at $1.0 \times 10^7$ cells per mouse into NODbdc mice, 7–14 days of age. Alternatively, NODscid mice were injected intravenously on 2–3 occasions at 2 week intervals with $1.0 \times 10^7$ insulin-specific T cell clones in HBSS per mouse per injection. Recipient mice were monitored for blood glucose measured by an ExacTech Blood Glucose Sensor (MediSense, Inc., Waltham, Mass.) and considered diabetic after three consecutive blood glucose values above 10 mmol/L.

NOD Mice Respond to B:9-23 and Tetanus Toxin Peptide p830-843 (TT:830-843) When Immunized With These Peptides Emulsified in Complete Freund's Adjuvant (CFA)

Figure 2B:
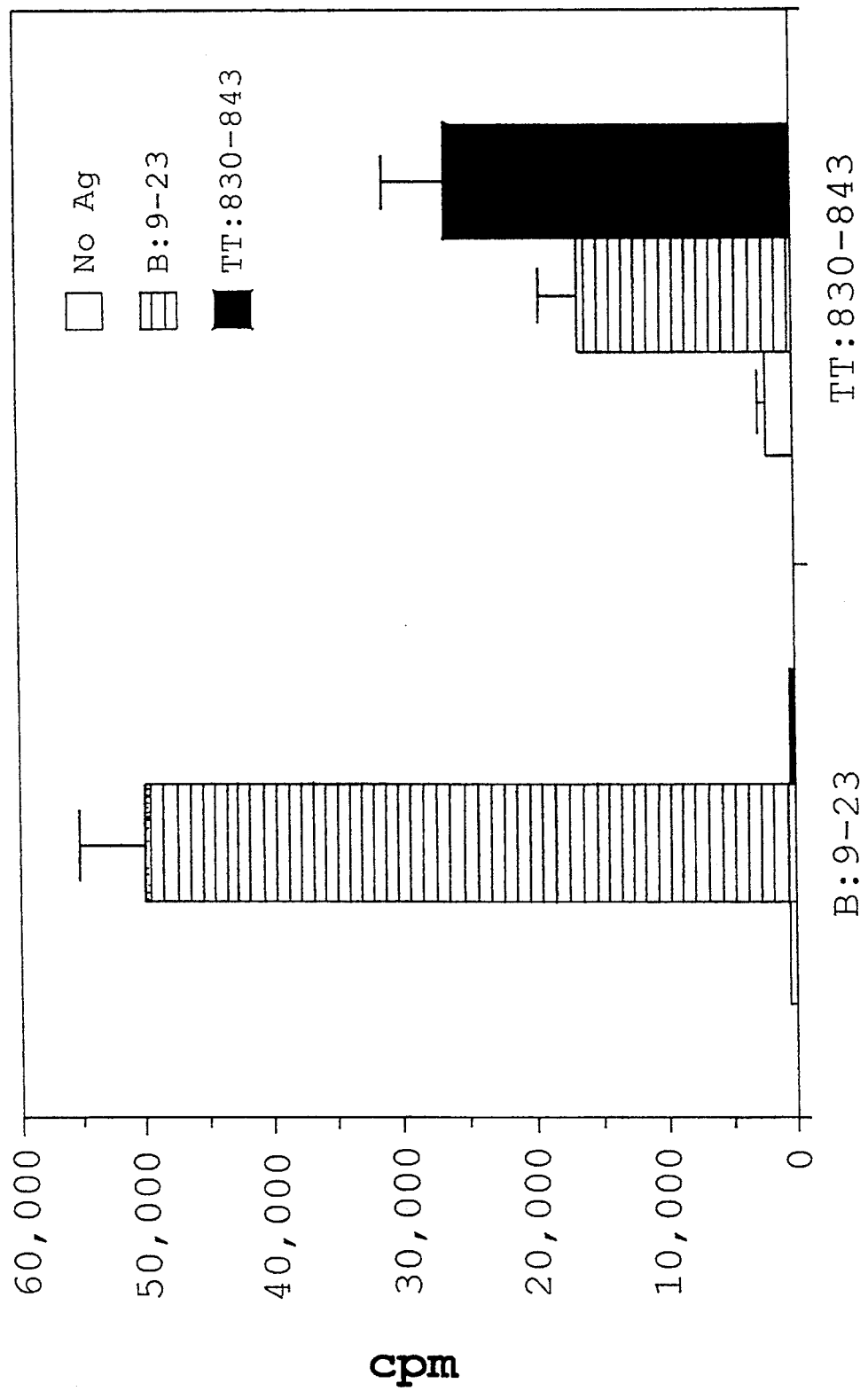
FIG. 2B is a graph showing the inguinal and periaortic lymph node cell ($1.0 \times 10^6$) responses of peptide immunized mice to 33 μg/ml B:9-23 (17.4 μM) or TT:830-843 (17.9 μM) in 0.2 ml supplemented Click's medium. The cultures were incubated for 5 days with a pulse of 0.5 mCi [$^3$H] thymidine added to each well 18 hours prior to harvest. The results are expressed as mean cpm for triplicate or quadruplicate wells.

The synthetic peptide TT:830-843 was selected as a control antigen [Panina et al., Eur. J. Immunol. 19: 2237 (1989); Demotz et al., J. Immunol. 142(2): 394 (1989)]. T cell responsiveness of NOD mice to B:9-23 and TT:830-843 (FIG. 2A) were determined by primed lymph node proliferation assays [Corradin et al., J. Immunol. 119: 1048 (1977)]. The results (FIG. 2B) indicate that NOD mice mount vigorous T cell responses to both of these peptides, confirming that TT:830-843 is an appropriate control antigen.

Figure 3A:
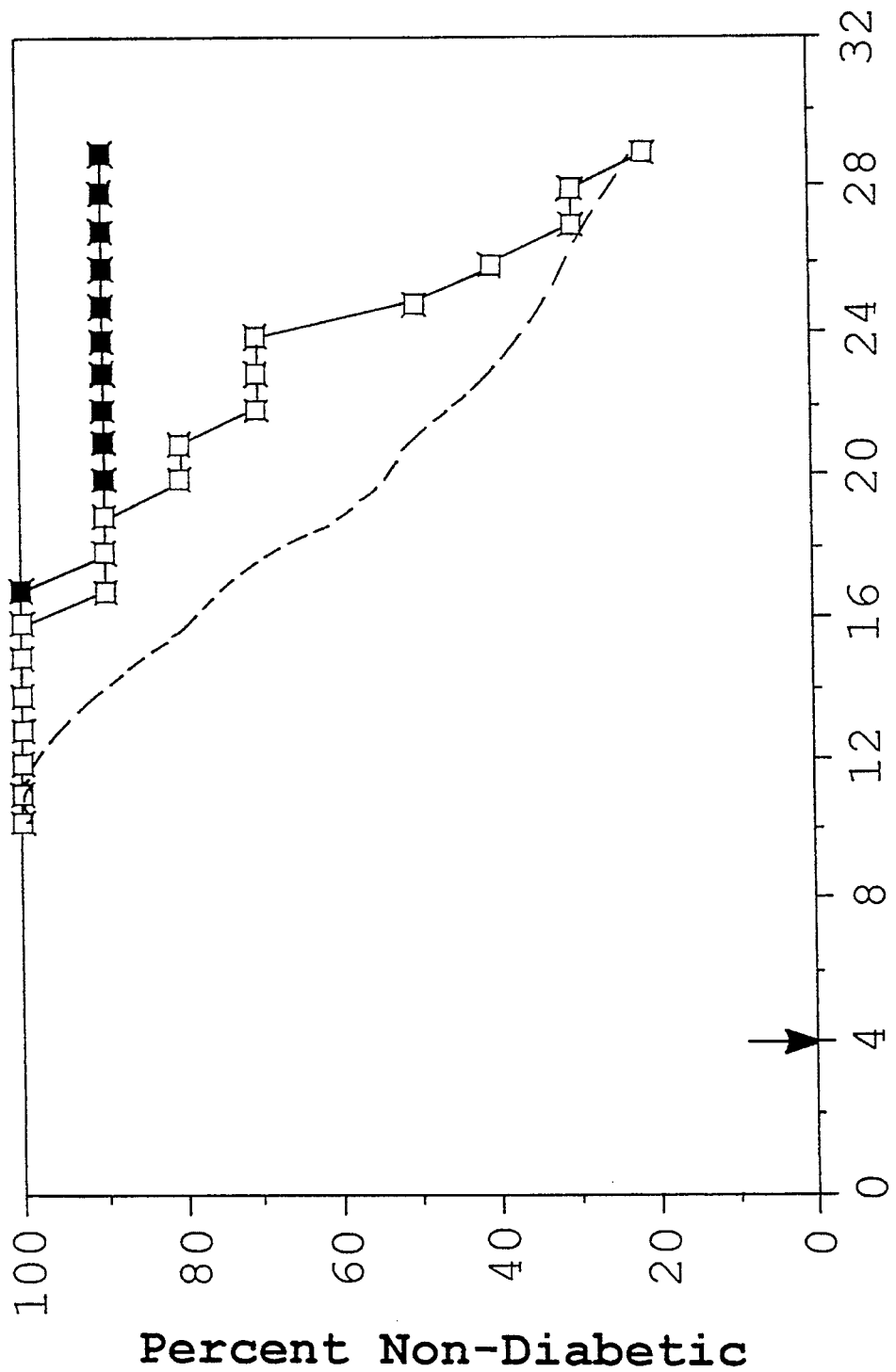
FIG. 3A is a graph showing the effect of subcutaneous injection of insulin peptide B:9-23 in Incomplete Freund's Adjuvant (IFA) on diabetes incidence in NOD mice. Four week old female NOD mice receiving subcutaneous B:9-23+IFA (n=10) (filled squares) show delayed onset (P=0.0168; Mann-Whitney U-test) and reduced frequency (P=0.0055; Fisher's exact) of diabetes when compared to litter mates receiving subcutaneous TT:830-843+IFA (n=10) (open squares). Arrow indicates time of subcutaneous.

Subcutaneous Administration of B:9-23 Emulsified in IFA Results in a Decrease in the Incidence of Diabetes in Female NOD Mice Groups of 4 week old female NOD mice were given a single subcutaneous injection of B:9-23 or TT:830-843 in IFA and monitored for development of diabetes. The results (FIG. 3A) that mice that received B:9-23 had a greatly reduced incidence of diabetes relative to the general incidence in the colony (P<0.00001 by Fisher's exact) and to TT:830-843 treated mice (P=0.0055).

Figure 3B:
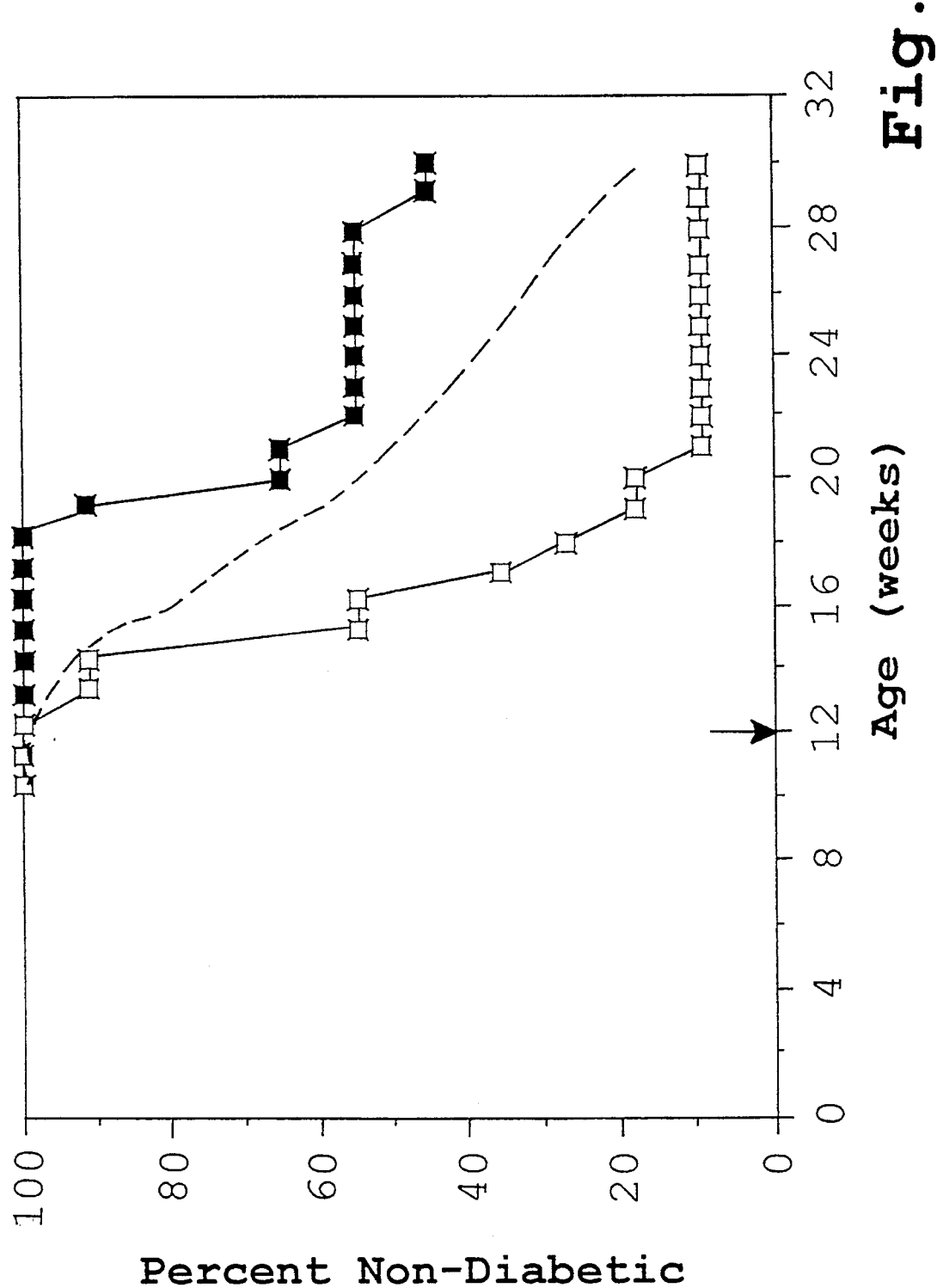
FIG. 3B is a graph showing the effect of intranasal administration of insulin peptide B:9-23 on diabetes incidence in NOD mice. Twelve week old female NOD mice receiving intranasal B:9-23 (n=11) (filled squares) show delayed onset of diabetes (P=0.0020; Mann-Whitney U-test) when compared to litter mates receiving intranasal TT:830-843 (n=11) (open squares). Arrow indicates time of intranasal treatment. Dashed line indicates incidence of diabetes among NODbdc females during 1993.

Intranasal Administration of B:9-23 Results in a Delay in the Onset of Diabetes in NOD Mice Twelve week old female NOD mice were used for intranasal administration of B:9-23. The results (FIG. 3B) indicate that intranasal B:9-23 resulted in a delay in the onset of diabetes compared to TT:830-843 treated control mice (P=0.002 by Mann Whitney U-test). In addition, a subgroup of mice exhibited a more prolonged delay in the onset of diabetes as indicated by the observation that 5 of the 11 B:9-23 treated mice have remained free of diabetes out to 30 weeks of age whereas 10 of 11 TT:830-843 treated mice were diabetic by 24 weeks of age.

The amino acid residues identified herein are preferably in the natural "L" isomeric form. However, residues in the "D" isomeric form can be substituted for any L-amino acid residue, as long as the desired functional property is retained by the peptide. $NH_2$ refers to the free amino group present at the amino terminus of a peptide. COOH refers to the free carboxy group present at the carboxy terminus of a peptide. In keeping with standard polypeptide nomenclature [*J. Biol, Chem.*, 260:14 (1983)] and adopted at 37 CFR §1.822(b)(2), abbreviations for amino acid residues are shown in Table 3:

TABLE 3

| SYMBOL | | |
|---|---|---|
| 1-Letter | 3-Letter | AMINO ACID |
| Y | Tyr | tryosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. In addition, the phrase "amino acid residue" is broadly defined to include modified and unusual amino acids, such as those listed in 37 CFR §1.822(b)(4), and are incorporated by reference. Furthermore, it should be noted that a dash at the beginning or end of an amino acid residue sequence indicates either a peptide bond to a further sequence of one or more amino acid residues or a covalent bond to a carboxyl or hydroxyl end group.

Thus, in another embodiment, the invention contemplates multimers or tandem repeats of the B:9-23 peptide, preferably held together by covalent bonds. The multimers may be dimers, trimers, tetramers, and the like.

It should be understood that a subject peptide need not be identical to the amino acid residue sequence of the B:9-23 peptide, so long as it includes the required sequence and is able to prevent type I diabetes as described herein.

A subject peptide includes any analog, fragment or chemical derivative of the B:9-23 peptide, so long as the peptide is capable of preventing type I diabetes. Therefore, a present peptide can be subject to various changes, substitutions, insertions, and deletions where such changes provide for certain advantages in its use. In this regard, a peptide according to this invention corresponds to, rather than is identical to, the B:9-23 peptide where one or more changes are made and it retains the ability to prevent type I diabetes.

The term "analog" includes any peptide having an amino acid residue sequence substantially identical to the B:9-23 peptide in which one or more residues have been conservatively substituted with a functionally similar residue and which displays the ability to prevent type I diabetes. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite inhibitory activity.

"Chemical derivative" refers to a subject peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides of the present invention also include any peptide having one or more additions and/or deletions or residues relative to the sequence of the B:9-23 peptide, so long as the requisite activity is maintained.

For example, the peptides of the present invention encompass the B:9-23 peptide having one or more amino acids added to the aminoterminus and/or carboxy-terminus.

The term "fragment" refers to any subject peptide having an amino acid residue sequence shorter than that of the B:9-23 peptide.

When a peptide of the present invention has a sequence that is not identical to the B:9-23 peptide, it is typically because one or more conservative or non-conservative substitutions have been made, usually no more than about 30 percent, more usually no more than 20 percent, and preferably no more than 10 percent of the amino acid residues are substituted.

Preferably, a peptide of this invention is further characterized by its ability to immunologically mimic an epitope (antigenic determinant) expressed by the B:9-23 peptide. Such a peptide is useful herein as a component in an inoculum for producing antibodies that immunoreact with the B:9-23 peptide.

As used herein, the phrase "immunologically mimic" in its various grammatical forms refers to the ability of a peptide of this invention to immunoreact with an antibody of the present invention that recognizes a conserved eiptope of the B:9-23 peptide.

Additional residues may also be added at either terminus for the purpose of providing a "linker" by which the peptides of this invention can be conveniently affixed to a label or solid matrix, or carrier. Preferably the linker residues do not form factor B:9-23 epitopes, i.e., are not similar is structure to B:9-23 peptide.

Labels, solid matrices and carriers that can be used with the peptides of this invention are described herein below.

Amino acid residue linkers are usually at least one residue and can be 40 or more residues, more often 1 to 10 residues, but do not form B:9-23 epitopes. Typical amino acid residues used for linking are tyrosine, cysteine, lysine, glutamic and aspartic acid, or the like. In addition, a subject peptide can differ, unless otherwise specified, from the sequence of B:9-23 by the sequence being modified by terminal-NH2 acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, a peptide of the present invention should be capable of inducing antibodies that immunoreact with peptides and fragments thereof that correspond to the B:9-23 peptide. In view of the well established principle of immunologic cross-reactivity, the present invention therefore contemplates antigenically related variants of the peptides corresponding to the B:9-23 peptide. An "antigenically related variant" is a subject peptide that is capable of including antibody molecules that immunoreact with a peptide and fragments thereof that correspond to the B:9-23 peptide.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

A peptide of the present invention, also referred to herein as a subject peptide, can be synthesized by any of the techniques that are known to those skilled in the peptide art. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final peptide.

The peptides or combination of peptides of the invention are used to prevent type I diabetes in mammals. While it is possible for the peptides to be administered alone, it is preferable to present it as a pharmaceutical composition, formulation or preparation. The peptides of the present invention, for use in pharmaceutical composition are manufactured under Current Good Manufacturing Practices (cGMP) as outlined in the United States Code of Federal Regulations (21 CFR 210, 211 and 820).

The formulations of the present invention, both for veterinary and for human use, comprise a peptide as described herein, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be present in unit dosage form and may be prepared by any method well-known in the pharmaceutical art.

All methods include the step of bringing into association the active ingredient with the carrier which constitutes one or more necessary ingredients. In general, the formulations are prepared by uniformly and intimately bringing into association the active ingredient with liquid carriers or finally divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferable isotonic with the blood of the recipient. Such formulations may be conveniently prepared by dissolving solid active ingredient in water containing physiologically compatible substances such as sodium chloride (e.g., 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferable incorporated in an amount of 0.11–10,000 parts by weight per part by weight of antibody. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferable in the range of 0.8–1.2. The pH of the aqueous solution is adjusted to be within the range of 5.0–9.0, preferably within the range of 6–8. In formulating the peptides of the present invention, anti-absorption agent may be used.

Additional pharmaceutical methods may be employed to control the duration of action. Controlled release preparations may be achieved through the use of polymer to complex or absorb the peptides or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the peptides, peptide analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacrylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The administration of the peptides of the present invention may be for either a prophylactic or therapeutic purpose. When provided prophylactically, the peptide is provided in advance of any symptom due to type I diabetes. The prophylactic administration of the peptide serves to prevent or attenuate any subsequent type I diabetes in a mammal. When provided therapeutically, the peptide is provided at (or shortly after) the onset of type I diabetes or at the onset of any symptom caused by type I diabetes. The therapeutic administration of the peptide serves to attenuate the type I diabetes.

The amount of active peptide will, for the in vivo treatment of mammalian species, of course, depend upon the severity of the condition being treated, the route of administration chosen, and the specific activity of the active peptides, and ultimately will be decided by the attending physician or veterinarian.

The active peptide may be administered by any route appropriate to the condition being treated including intravenous, intraperitoneal, intramuscular, subcutaneous, oral, nasal and the like. It will be readily appreciated by those skilled in the art that the preferred route will very with the condition being treated.

The following example is presented to illustrate the present invention and to assist one of ordinary skill in making and using the same. The example is not intended in any way to otherwise limit the scope of the invention.

EXAMPLE

Administration of Insulin Peptide

B:9-23

NODbdc mice were obtained from the colony at the Barbara Davis Center and maintained under specific pathogen-free conditions. Reverse-phase HPLC purified insulin peptide B:9-23 (FIG. 2A) and synthetic peptide TT:830-843 (FIG. 2A) [Panina et al., *Eur. J. Immunol.* 19: 2237 (1989); Demotz et al., *J. Immunol.* 142(2): 394 (1989)] were obtained for immunization and intranasal administration to female NOD mice (Molecular Resources Center, National Jewish Hospital, Denver, Colo.).

Mice were immunized with 50 µg of either B:9-23 or TT:830-843 emulsified in CFA (50 µl total volume) at the base of the tail (Corradin et al., *J. Immunol.* 119: 1048 (1977)]. After two weeks, the TT:830-843 immunized mice were boosted with 50 µg TT:830-843 in IFA. After at least 7 days post immunization the draining lymph nodes (inguinal and periaortic) were removed and cell suspensions prepared. These cell suspensions were washed and cultured in triplicate or quadruplicate at $1.0 \times 10^6$ cells per well in 96 well microculture plates in Click's medium supplemented to 0.5% with normal mouse serum or to 1% with Nutridoma SP (Boehringer Mannheim, Indianapolis, Ind.) and the indicated peptide as antigen. These cultures were incubated at 37° C. for 5 days with a pulse of 0.5 µCi$^3$HTdr 18 hours prior to harvest.

Four week old female NODbdc mice were divided into experimental and control groups and given a single subcutaneous injection of 100 µg of either B:9-23 or TT:830-843 in IFA. The mice were monitored weekly for blood glucose (ExachTech Blood Glucose Sensor, MediSense, Inc., Waltham, Mass.) and considered diabetic after three consecutive values above 10 mmol/L.

Twelve week old female NODbdc litter mates were divided within litters into experimental and control groups. As described previously [Hoyne et al., *J. Exp. Med.* 178: 1783 (1993)], the mice were lightly anesthetized and administered 40 µg of either B:9-23 or TT:830-843 in 20 µl PBS (20 µg in 10 µl per nostril) intranasally on three consecutive days. The mice were monitored for diabetics as described above.

Administration of peptide B:9-23 to mice, either subcutaneously in IFA or intranasally in saline, resulted in a delay in the onset and a decrease in the incidence of diabetes relative to mice given a control peptide, TT:830-843. The control peptide TT:830-843, which is immunogenic in NOD mice, was without effect by either route.

All references referred to herein are incorporated by reference. As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the example contained in the foregoing description.

What is claimed is:

1. A peptide having the amino acid sequence Ser-His-Leu-Val-Glu-Ala-Leu-Tyr-Leu-Val-Cys-Gly-Glu-Arg-Gly (SEQ ID NO:1) of the B chain of insulin, said peptide characterized by acting as a tolerogen for preventing type I diabetes.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:1:

Ser His Leu Val Glu Ala Leu Tyr Leu Val Cys Gly Glu Arg Gly
1               5                   10                  15